United States Patent
Devellian et al.

(10) Patent No.: US 8,231,604 B2
(45) Date of Patent: Jul. 31, 2012

(54) AIR EMBOLIZATION PREVENTION SYSTEM

(75) Inventors: Carol A. Devellian, Topsfield, MA (US); Steven W. Opolski, Carlisle, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 1672 days.

(21) Appl. No.: 10/925,839

(22) Filed: Aug. 25, 2004

(65) Prior Publication Data

US 2005/0113805 A1 May 26, 2005

Related U.S. Application Data

(60) Provisional application No. 60/523,565, filed on Nov. 20, 2003.

(51) Int. Cl.
*A61M 25/16* (2006.01)
(52) U.S. Cl. ..................... 604/539
(58) Field of Classification Search .............. 604/500, 604/507, 508, 164.01, 167.01, 167.02, 167.03, 604/533, 523, 539; 606/108
See application file for complete search history.

(56) References Cited

U.S. PATENT DOCUMENTS

| | | | |
|---|---|---|---|
| 4,323,071 A | 4/1982 | Simpson et al. | |
| 4,531,937 A * | 7/1985 | Yates | 604/539 |
| 4,545,390 A | 10/1985 | Leary | |
| 4,682,980 A * | 7/1987 | Suzuki | 604/122 |
| 4,684,363 A | 8/1987 | Ari et al. | |
| 4,689,047 A | 8/1987 | Bauer | |
| 4,692,200 A | 9/1987 | Powell | |
| 4,714,461 A | 12/1987 | Gabel | |
| 4,759,751 A | 7/1988 | Gabel et al. | |
| 4,784,644 A | 11/1988 | Sawyer et al. | |
| 5,032,116 A * | 7/1991 | Peterson et al. | 604/168.01 |
| 5,066,284 A * | 11/1991 | Mersch et al. | 604/168.01 |
| 5,224,933 A | 7/1993 | Bromander | |
| 5,334,153 A | 8/1994 | McIntyre et al. | |
| 5,935,094 A * | 8/1999 | Zupkas | 604/8 |
| 6,213,996 B1 * | 4/2001 | Jepson et al. | 604/533 |
| 6,245,045 B1 | 6/2001 | Stratienko | |
| 6,254,611 B1 | 7/2001 | Vrba | |
| 2002/0103473 A1 | 8/2002 | Roychowdhury et al. | |
| 2002/0111645 A1 | 8/2002 | Wang et al. | |
| 2003/0212360 A1 | 11/2003 | Shkolnik | |

FOREIGN PATENT DOCUMENTS

| | | |
|---|---|---|
| EP | 0 495 497 | 7/1992 |
| JP | 2003-154009 | 5/2003 |

OTHER PUBLICATIONS

International Searching Authority, "International Search Report," PCT Application No. PCT/US2004/027550, mailed on Dec. 30, 2004, 5 pgs.
International Searching Authority, "Written Opinion of the International Searching Authority," PCT Application No. PCT/US2004/027550, mailed on Dec. 30, 2004, 8 pgs.

* cited by examiner

*Primary Examiner* — Christopher D Koharski
(74) *Attorney, Agent, or Firm* — DLA Piper LLP (US)

(57) ABSTRACT

The invention generally relates to an intravascular catheter that includes a proximal hub and a distal elongated tubular member. In one embodiment, the hub is designed to mitigate the introduction of air into a patient's vasculature during the delivery of a second device through the catheter into the patient's body.

14 Claims, 6 Drawing Sheets

AIR EMBOLIZATION PREVENTION SYSTEM

CROSS-REFERENCE TO RELATED APPLICATION

This application incorporates by reference, and claims priority to and the benefit of, U.S. provisional application Ser. No. 60/523,565, which was filed on Nov. 20, 2003.

TECHNICAL FIELD

The invention generally relates to a catheter, and related methods, for introducing a device into the body of a patient. More particularly, the invention relates to a catheter and related methods that mitigate, during an interventional procedure, the passage of air through the catheter into the patient's body.

BACKGROUND INFORMATION

An intravascular catheter is often used by cardiologists and/or radiologists in intravascular procedures. Typically, during such procedures, the catheter is first inserted into a patient's body and a second device is then inserted into a lumen of the catheter and, optionally, also into the patient's body.

A risk inherent with such interventional procedures is the inadvertent introduction of air into the catheter lumen when the second device is inserted therein. With the catheters known in the art, the introduced air may find its way into the patient's vascular system and thereafter block, for example, a vessel in the lungs, the brain, or the heart. Adverse consequences, such as, for example, acute pulmonary embolism, myocardial infarction, stroke, and possibly death, can therefore result.

Thoroughly flushing the lumens of the catheters known in the art is a standard procedure used to prevent the introduction of air into the patient's vascular system. Nevertheless, despite flushing, even the most experienced physician, carefully using the proper technique for the interventional procedure in question, may still introduce air into the patient's vascular system.

Improved intravascular catheters that mitigate the introduction of air into the patient's vascular system are, therefore, needed.

SUMMARY OF THE INVENTION

The invention generally relates to an intravascular catheter that includes a proximal hub and a distal elongated tubular member. Typically, the hub remains outside a patient's body during a clinical procedure, while the elongated tubular member is inserted into the patient's vasculature. The hub is designed to mitigate the introduction of air into the patient's vasculature during the delivery of a second device through the inventive catheter into the patient's body. The second device may be, for example, another catheter (e.g., an angiocatheter), a stent, a filter, a septal occluder, a device for obliterating the left atrial appendage, a suture, a staple, or an adhesive.

According to one feature, the hub of the inventive intravascular catheter includes a reservoir for trapping air bubbles that have been introduced into the hub, thereby impeding the air bubbles from migrating throughout the catheter and into the patient's vascular system. According to another feature, the hub includes an air permeable porous member, either in addition to, or as an alternative to, the reservoir. The air permeable porous member allows air bubbles that have been introduced into the hub to escape the hub into the surrounding environment outside the patient. Air bubbles inadvertently introduced into the catheter are prevented, therefore, from finding their way into the patient's vascular system.

In one aspect, the invention relates to an intravascular catheter. The intravascular catheter includes an elongated tubular member and a hub. The elongated tubular member includes a proximal end, a distal end, and a lumen that extends from the proximal end to the distal end. The hub includes a first end, a second end, and a reservoir that includes at least one pocket. The second end of the hub is coupled to the proximal end of the elongated tubular member. The hub reservoir extends from the first end of the hub to the second end of the hub, and the at least one pocket of the hub reservoir is partially shielded from the lumen of the elongated tubular member.

Various embodiments of this aspect of the invention include the following features. The hub may include an air permeable membrane positioned, for example, through a surface of the hub between the first end and the second end of the hub, or through a surface of the hub at at least one of the first end and the second end of the hub. Moreover, the hub may include a valve and/or a flushing port. Additionally, the hub may be made of a transparent material. In yet another embodiment, at least a portion of the hub reservoir has a cross-sectional diameter that is greater in size than a cross-sectional diameter of the lumen of the elongated tubular member.

In still another embodiment, the hub includes a first sealing gland positioned, for example, at the first end of the hub. At least a portion of the distal surface of the first sealing gland may be angled towards the first end of the hub. Moreover, in one embodiment, the first sealing gland includes a plurality of pores. In yet another embodiment, the hub includes a second sealing gland positioned, for example, at the second end of the hub. At least a portion of the proximal surface of the second sealing gland may be angled towards the second end of the hub. In a further embodiment, the hub includes an opening, which is in fluid communication with the hub reservoir, at the first end of the hub.

In another aspect, the invention provides an intravascular catheter. The intravascular catheter includes an elongated tubular member and a hub. The elongated tubular member includes a proximal end, a distal end, and a first lumen that extends from the proximal end to the distal end. The hub includes a first end, a second end coupled to the proximal end of the elongated tubular member, a second lumen that extends from the first end to the second end of the hub, and an air permeable porous member.

In one embodiment of this aspect of the invention, the air permeable porous member is a gland positioned at the first end of the hub. In another embodiment, the air permeable porous member is a membrane positioned between the first end and the second end of the hub. The air permeable porous member may be coated with or impregnated with, for example, a low thrombogenicity material or drug, such as, for example, heparin or hyaluronic acid.

In yet other aspects, the invention provides methods for inserting an intravascular catheter into the body of a patient. The methods include providing an intravascular catheter as described above and inserting the intravascular catheter into a vessel of the patient.

The foregoing and other objects, aspects, features, and advantages of the invention will become more apparent from the following description taken in conjunction with the accompanying drawings.

BRIEF DESCRIPTION OF THE DRAWINGS

In the drawings, like reference characters generally refer to the same parts throughout the different views. Also, the draw

DESCRIPTION

In one aspect, the invention features an intravascular catheter that includes a hub. The hub is designed to mitigate the introduction of air into a patient's vasculature when, for example, another catheter (e.g., an angiocatheter), a stent, a filter, a septal occluder, a device for obliterating the left atrial appendage, a suture, a staple, or an adhesive is delivered through the intravascular catheter into the patient's body.

Figure 1:
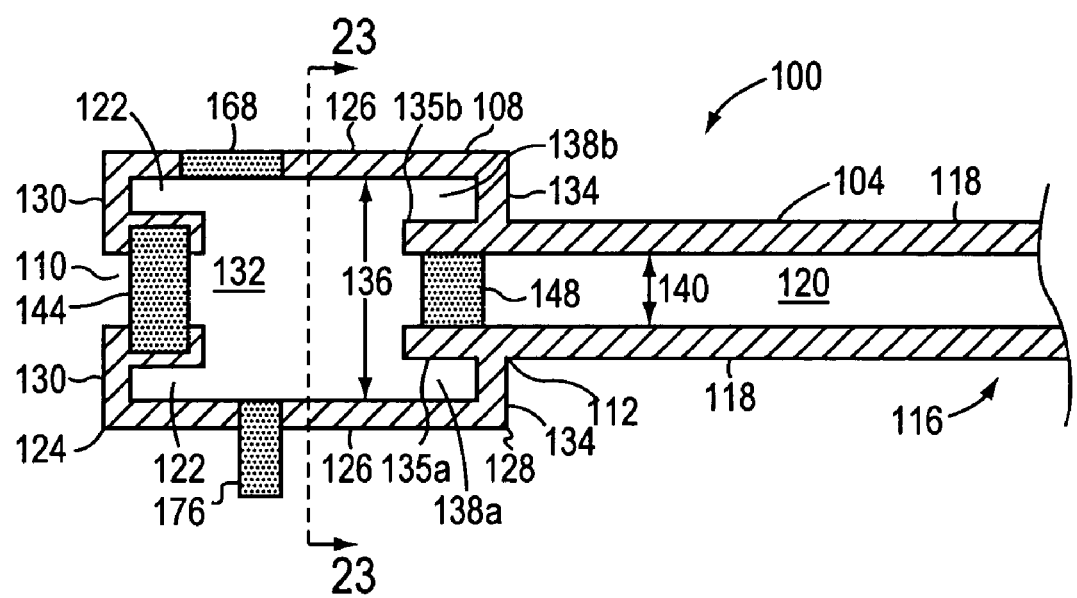
- FIG. 1 is a schematic cross-sectional view of a portion of an intravascular catheter according to an illustrative embodiment of the invention.

FIG. 1 depicts a portion of an intravascular catheter 100 according to an illustrative embodiment of the invention. As shown in the illustrative embodiment, the intravascular catheter 100 includes an elongated tubular member 104 and a hub 108. The elongated tubular member 104 includes a proximal end 112 (i.e., an end that is closest to a physician when the physician is using the intravascular catheter 100), an opposite, distal end 116, and a lumen 120 that extends from the proximal end 112 to the distal end 116. For its part, in one embodiment, the hub 108 includes a proximal first end 124, an opposite, distal second end 128, and a reservoir 132 that extends from the first end 124 to the second end 128. The hub 108 also includes a side wall 126 between the first end 124 and the second end 128, a first external surface 130 at its first end 124, and a second external surface 134 at its second end 128.

The second end 128 of the hub 108 is joined to the proximal end 112 of the elongated tubular member 104. In one embodiment, the hub 108 and the elongated tubular member 104 are, in fact, one integral component formed by, for example, injection molding. In another embodiment, the hub 108 and the elongated tubular member 104 are separate components joined together by, for example, an adhesive or thermal bonding.

Referring still to FIG. 1, at least a portion of the illustrative reservoir 132 has a cross-sectional diameter 136 that is greater in size than a cross-sectional diameter 140 of the lumen 120 of the elongated tubular member 104. Moreover, the illustrative reservoir 132 includes, in one embodiment, at least one pocket 138. For example, the reservoir 132 includes, as shown, two pockets 138a and 138b. The pockets 138a, 138b are partially shielded from the lumen 120 of the elongated tubular member 104 by hub extensions 135a, 135b, respectively. The hub extensions 135a, 135b are incomplete partitions that extend, for example, from the second end 128 of the hub 108 into the reservoir 132 in a direction towards the first end 124 of the hub 108.

Figure 2:
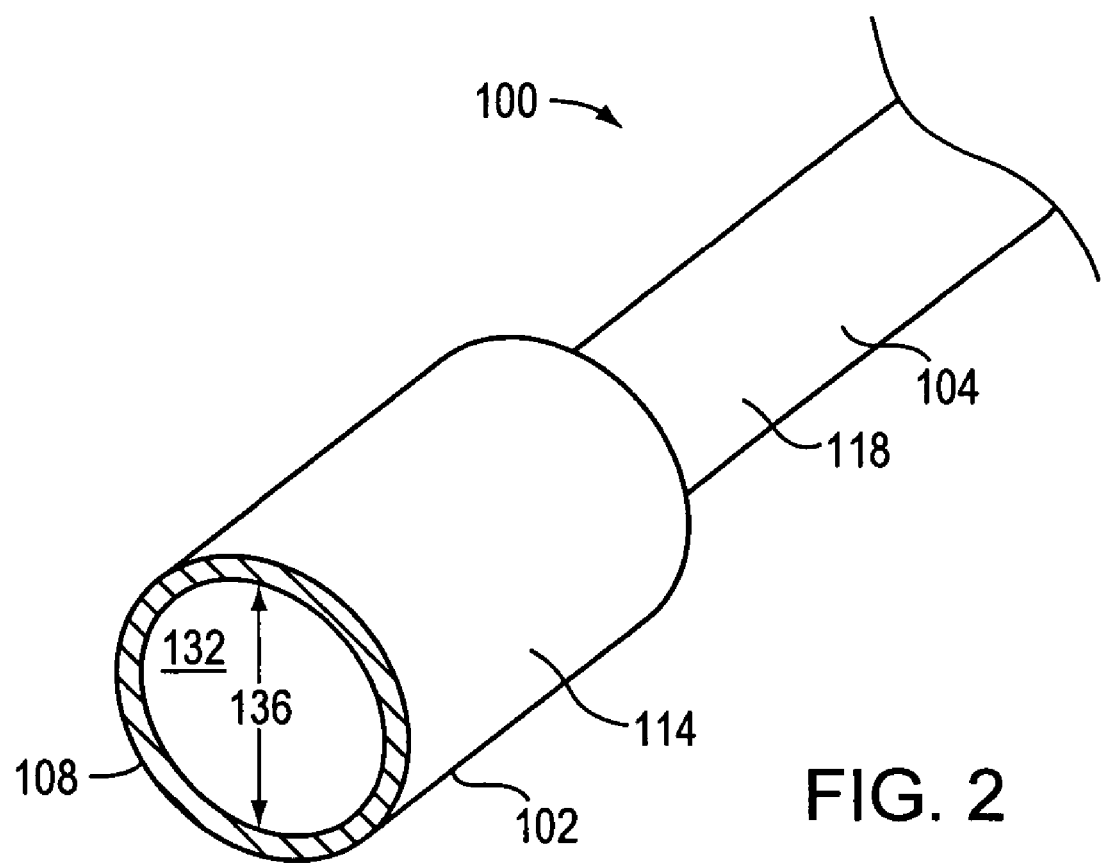
FIG. 2 is a schematic cross-sectional perspective view of the hub of the intravascular catheter portion illustrated in FIG. 1, taken at a line 23-23 of FIG. 1, according to an illustrative embodiment of the invention.

FIG. 2 depicts a schematic cross-sectional perspective view of the hub 108 of the intravascular catheter 100 illustrated in FIG. 1, taken at a line 23-23 of FIG. 1, according to an illustrative embodiment of the invention. The exemplary hub 108 depicted in FIG. 2 includes a cylindrical portion 102 whose outer circumference 114 is greater than, and projects beyond, an outer circumference 118 of the elongated tubular member 104. The reservoir 132 of the hub 108 also projects beyond the outer circumference 118 of the elongated tubular member 104, such that the cross-sectional diameter 136 of the reservoir 132 is greater in size than the cross-sectional diameter 140 of the lumen 120 of the elongated tubular member 104 (see FIG. 1).

Figure 3:
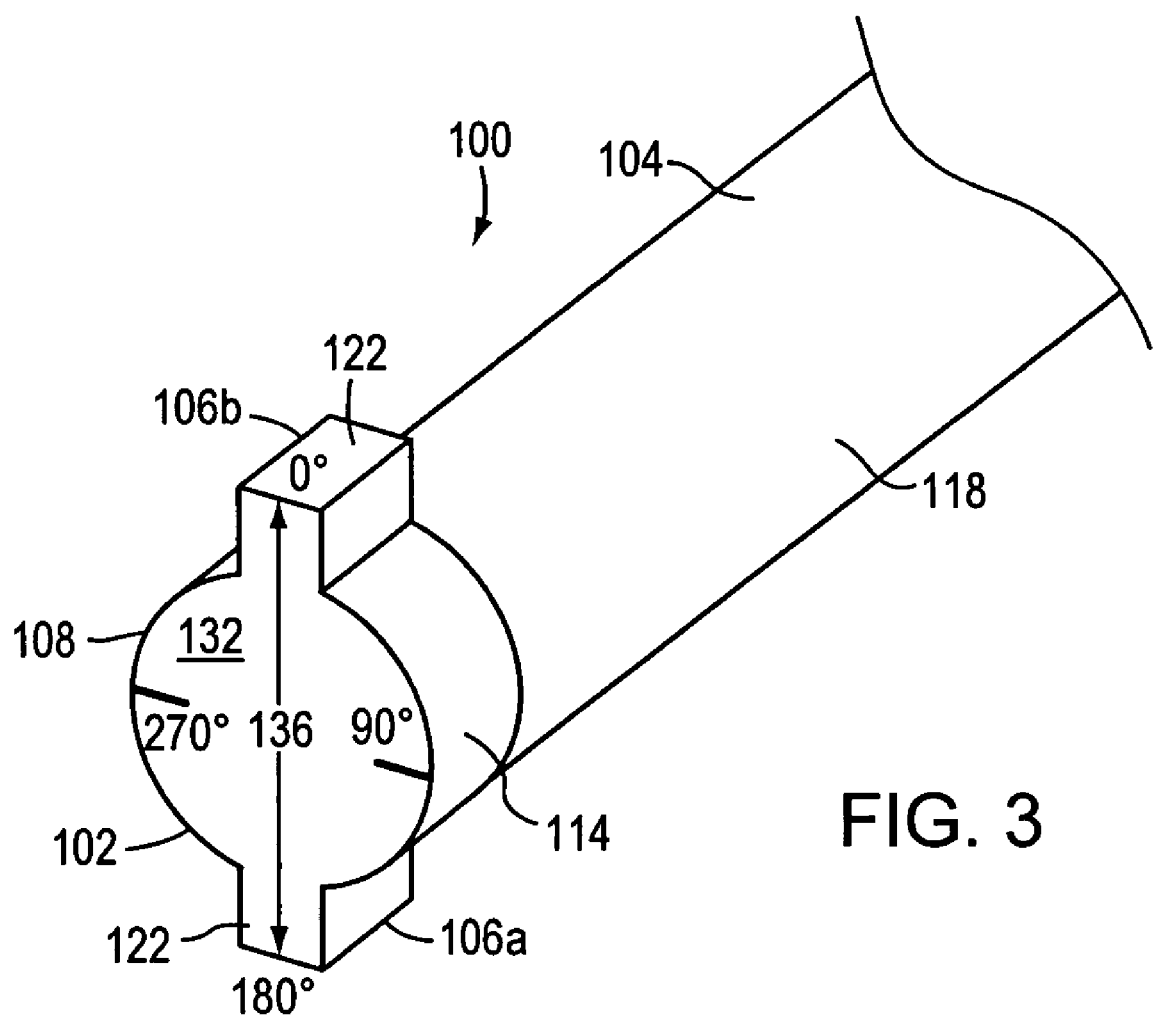
FIG. 3 is a schematic cross-sectional perspective view of the hub of the intravascular catheter portion illustrated in FIG. 1, taken at the line 23-23 of FIG. 1, according to another illustrative embodiment of the invention.

FIG. 3 depicts a schematic cross-sectional perspective view of the hub 108 of the intravascular catheter 100 illustrated in FIG. 1, taken at the line 23-23 of FIG. 1, according to yet another illustrative embodiment of the invention. The exemplary hub 108 depicted in FIG. 3 includes a cylindrical portion 102 and one or more projections 106, for example projections 106a and 106b. The outer circumference 114 of the cylindrical portion 102 of the hub 108 is co-extensive with the outer circumference 118 of the elongated tubular member 104. The reservoir 132 extends into the one or more projections 106, which project beyond the outer circumference 118 of the elongated tubular member 104. Referring to FIGS. 1 and 3, the cross-sectional diameter 136 of the reservoir 132 is, in an area of the reservoir 132 that includes, and that extends into, the one or more projections 106, greater in size than the cross-sectional diameter 140 of the lumen 120 of the elongated tubular member 104.

Referring still to FIG. 3, the one or more projections 106 may be distributed at any location(s) around the outer circumference 114 of the cylindrical portion 102. For example, one projection 106b may be distributed at 0° and one projection 106a may be distributed at 180°, as illustrated in FIG. 3. In use, a physician may orient at least one projection 106 that extends beyond the outer circumference 118 of the elongated tubular member 104 away from the earth's center of gravity (e.g., projection 106b, as illustrated). As explained below, the reservoir 132 will be filled by blood. Thus, by positioning, for example, the projection 106b away from the earth's center of gravity, air introduced into the reservoir 132 will migrate away from the earth's center of gravity and into the portion of the reservoir 132 located in the projection 106b.

Figure 4:
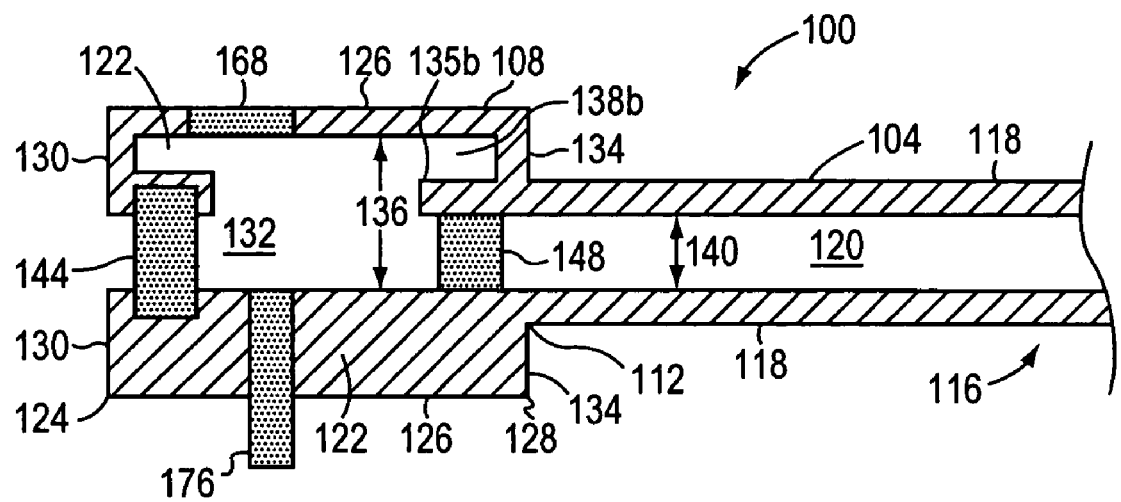
FIG. 4 is a schematic cross-sectional view of a portion of an intravascular catheter according to another illustrative embodiment of the invention.

Referring again to FIGS. 1 and 3, in one embodiment of the intravascular catheter 100 according to the invention, the hub 108 and the reservoir 132 each include two portions 122 that extend beyond the outer circumference 118 of the elongated tubular member 104. Alternatively, in another embodiment of the intravascular catheter 100, referring now to FIG. 4, the hub 108 includes two portions 122 that extend beyond the outer circumference 118 of the elongated tubular member 104. The reservoir 132 includes but one portion 122 that extends beyond the outer circumference 118 of the elongated tubular member 104.

Figure 5:
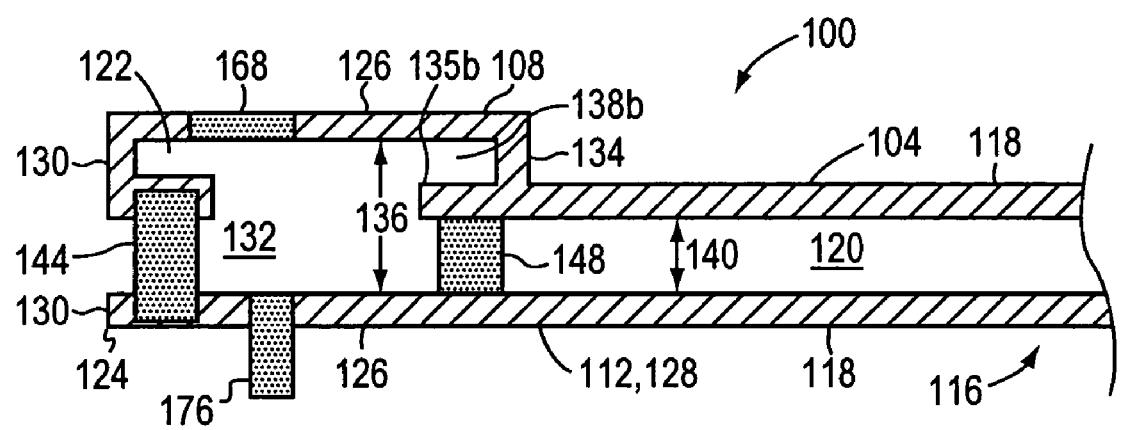
FIG. 5 is a schematic cross-sectional view of a portion of an intravascular catheter according to yet another illustrative embodiment of the invention.

In yet another embodiment, referring now to FIG. 5, the hub 108 and the reservoir 132 each include only one portion 122 that extends beyond the outer circumference 118 of the elongated tubular member 104. Alternatively, in further embodiments, the hub 108 and the reservoir 132 may each include any number of portions 122 that extend beyond the outer circumference 118 of the elongated tubular member 104.

In use, a physician may orient at least one portion 122 of the reservoir 132 that extends beyond the outer circumference 118 of the elongated tubular member 104 away from the earth's center of gravity. Accordingly, air introduced into the reservoir 132 will migrate away from the earth's center of gravity, through the blood located in the reservoir 132, and into the portion 122 of the reservoir 132 that is oriented away from the earth's center of gravity.

Other shapes and configurations of the hub 108 and/or reservoir 132 are also possible. The invention is not limited to the illustrated shapes and configurations of the hub 108 and reservoir 132.

Figure 6:
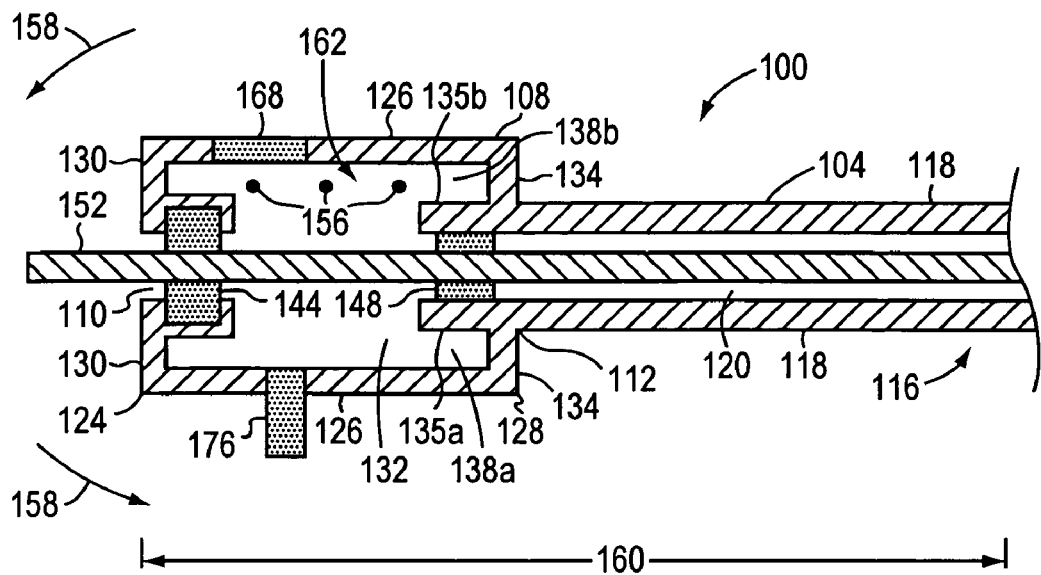
FIG. 6 is a schematic cross-sectional view of a portion of a device inserted, according to an illustrative embodiment of the invention, into the illustrative intravascular catheter portion of FIG. 1.

FIG. 6 depicts a portion of an exemplary device 152 inserted, according to an illustrative embodiment of the invention, into the illustrative intravascular catheter 100, after the intravascular catheter 100 has been inserted into the patient's body. The exemplary device 152 may be, for example, another catheter (e.g., an angiocatheter), a stent, a filter, or a front-end loader for delivering a device, such as a septal occluder, a device for obliterating the left atrial appendage, a suture, a staple, or an adhesive, to the heart of a patient.

Referring both to FIG. 1 and FIG. 6, in one embodiment, the hub 108 includes an opening 110 at its first end 124. Another feature of the hub 108 is, for example, a first sealing gland 144, which may also be positioned at the first end 124 of the hub 108. The opening 110 of the hub 108 is in fluid communication with the reservoir 132 of the hub 108. In one embodiment, the opening 110 of the hub 108 is in fluid communication with the reservoir 132 of the hub 108 through the first sealing gland 144. The exemplary first sealing gland 144 may be constructed of, for example, a resilient elastomer material that seals around the device 152 when the device 152 is inserted through the opening 110 of the hub 108 into the reservoir 132 of the hub 108.

Optionally, referring still to FIGS. 1 and 6, the exemplary hub 108 also includes a second sealing gland 148 positioned, for example, at the second end 128 of the hub 108. Like the first sealing gland 144, the exemplary second sealing gland 148 may be constructed of, for example, a resilient elastomer that seals around the device 152 when the device 152 is inserted into the lumen 120 of the elongated tubular member 104 of the intravascular catheter 100.

Figure 7:
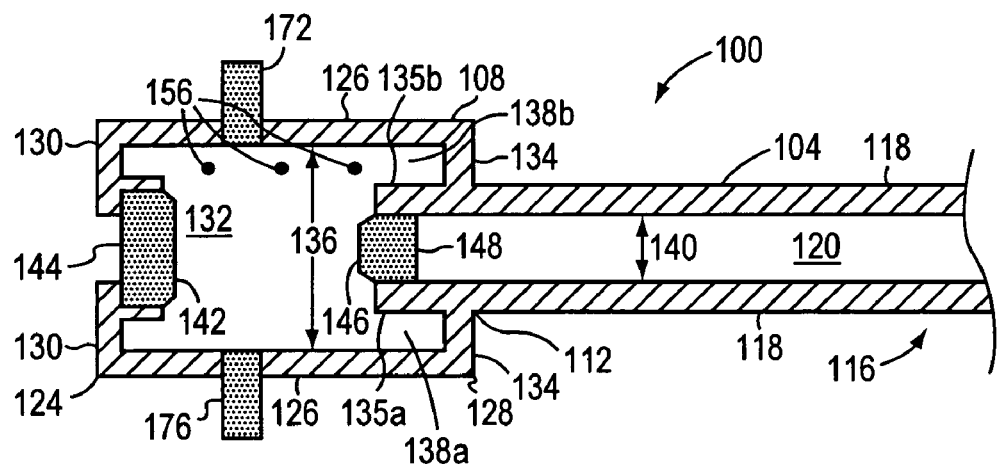
FIG. 7 is a schematic cross-sectional view of a portion of an intravascular catheter according to still another illustrative embodiment of the invention.

In one embodiment, as depicted in FIG. 7, at least a portion of the distal surface 142 of the first sealing gland 144 angles towards the first end 124 of the hub 108 and/or at least a portion of the proximal surface 146 of the second sealing gland 148 angles towards the second end 128 of the hub 108. The angles to the surfaces 142, 146 promote the passage of air bubbles 156 away from the center of the hub 108 towards the periphery of the hub 108.

Any combinations of sealing glands and positions of sealing glands, including the absence of a second sealing gland 148, is contemplated by the invention. The combinations of sealing glands and positions of sealing glands are not limited to those disclosed herein.

Referring again to FIG. 6, according to the invention, air bubbles 156 introduced into the intravascular catheter 100, when the device 152 is inserted therein, are trapped by the reservoir 132 and prevented from migrating distal to the second end 128 of the hub 108 into the lumen 120 of the elongated tubular member 104. The air bubbles 156 are thereby impeded from traversing distally through the lumen 120 of the elongated tubular member 104 into the patient's vascular system.

In another aspect, the invention provides a method for performing an interventional procedure that minimizes the risk of introducing a gas (e.g., air) into a patient's cardiovascular system. With reference still to FIG. 6, in one embodiment, the physician inserts the intravascular catheter 100 into the patient's body, while maintaining a long axis 160 of a proximal portion of the intravascular catheter 100 substantially horizontal. The physician then inserts the device 152 into the reservoir 132 of the hub 108 and advances the device 152 into the lumen 120 of the elongated tubular member 104. The patient's blood fills the reservoir 132 of the hub 108. Consequently, air bubbles 156 that were introduced into the hub 108 by inserting the device 152 therein, having a smaller density than the patient's blood, immediately migrate towards a top portion 162 of the reservoir 132 (i.e., away from the earth's center of gravity).

In one embodiment, during an interventional procedure, the air bubbles 156 are retained in the top portion 162 of the reservoir 132. For example, after having inserted the device 152 into the intravascular catheter 100, the physician rotates the intravascular catheter 100 from the position depicted in FIG. 6 in the direction indicated by arrows 158. As a result, the air bubbles 156 are trapped by the pocket 138b and are impeded from entering the lumen 120 of the elongated tubular member 104.

Optionally, to further ensure that the air bubbles 156 do not migrate into the lumen 120 of the elongated tubular member 104, the hub 108 further includes the second sealing gland 148 that is positioned at the second end 128 of the hub 108. In one such embodiment, the second sealing gland 148 is impermeable to air.

The hub 108, during the course of an interventional procedure, remains outside the patient's body. Accordingly, in another embodiment, the hub 108 includes an air permeable membrane 168 positioned, for example as illustrated in FIGS. 1 and 6, through the side wall 126 of the hub 108. Alternatively, the air permeable membrane 168 may be positioned through the first external surface 130 at the first end 124 of the hub 108 (not shown) or through the second external surface 134 at the second end 128 of the hub 108 (not shown). The air permeable membrane 168 passively releases (i.e., without any physician actuation) the air bubbles 156 trapped by the reservoir 132 into the surrounding environment outside the patient. To operate as such, the air permeable membrane 168 may be fabricated from a porous material. The porous material may be, for example, any polymer foam fabricated from material such as silicone, polyurethane, and/or a thermoplastic elastomer (e.g., styrene-ethylene-butadiene-styrene (SEBS)). Alternatively, the porous material may be any polymer film or fabric, such as, for example, woven or knitted polyester, expanded polytetrafluoroethylene (ePTFE) (i.e., GORE-TEX®, which is manufactured by W. L. Gore & Associates, Inc. of Newark, Del.), polyethyle-teraphalate film, polyethylene film, and/or polyvinyl alcohol (PVA) film.

In one embodiment, the pore sizes in the air permeable membrane 168 are large enough to permit the air bubbles 156 to pass therethrough, but are small enough to prevent blood from permeating through the air permeable membrane 168. Specifically, the pore sizes are smaller than the size of red blood cells and white blood cells, but larger than the air molecules forming the air bubbles 156. The pore sizes may be, for example, in the range of about 0.01 µm to about 4.0 µm, preferably about 0.1 µm to about 1.0 µm.

In another embodiment, the air permeable membrane 168 is coated or impregnated with a low thrombogenicity material. For example, the air permeable membrane 168 may be coated and/or impregnated with heparin, hyaluronic acid, and/or another anti-thrombotic coating, agent, mammalian genetic and recombinant genetic material, or drug.

Like the air permeable membrane 168, in one embodiment according to the invention, the above-described first sealing gland 144 is fabricated from a porous material that includes a plurality of pores. The porous material and the pore sizes may be, for example, of the type and size described above for the air permeable membrane 168. Accordingly, the first sealing gland 144 may also passively release (i.e., without any physician actuation) the air bubbles 156 trapped in the reservoir 132 into the surrounding environment outside the patient, while maintaining blood inside the intravascular catheter 100. In a particular embodiment, the first sealing gland 144 includes a coating or is impregnated with a low thrombogenicity material, such as, for example, the materials listed above for the air permeable membrane 168.

FIG. 7 depicts a portion of an intravascular catheter 100 according to another illustrative embodiment of the invention. In this embodiment, the hub 108 includes an air release valve 172 to release the air bubbles 156 trapped in the reservoir 132, as described above, into the surrounding environment outside the patient. The air release valve 172 may be positioned through the side wall 126 of the hub 108, as illustrated in FIG. 7, through the first external surface 130 at the first end 124 of the hub 108 (not shown), or through the second external surface 134 at the second end 128 of the hub 108 (not shown). In one embodiment, the air release valve 172 requires manual actuation. For example, the air release valve 172 is a one way valve which includes a button that is pushed to release the trapped air bubbles 156 from the reservoir 132 into the surrounding environment outside the patient. Alternatively, the air release valve 172 is a passive valve that automatically operates without manual actuation (e.g., a one way passive valve, such as a check valve).

In yet another embodiment (not shown), the hub 108 includes both the air permeable membrane 168 and the air release valve 172. In still another embodiment (not shown), the hub 108 includes more than one air permeable membrane 168 and, additionally or alternatively, more than one air release valve 172.

In another embodiment, referring now to FIGS. 1, 6, and 7, the hub 108 includes a flushing port 176. As shown, the exemplary flushing port 176 is located through the side wall 126 of the hub 108. Alternatively, the flushing port 176 is located through the first external surface 130 of the hub 108 (not shown) or through the second external surface 134 of the hub 108 (not shown). In another embodiment (not shown), the hub 108 includes more than one flushing port 176, each one of which is located through the side wall 126, the first external surface 130, or the second external surface 134. Prior to placing the intravascular catheter 100 into the body of a patient, the hub 108 of the intravascular catheter 100 is flushed by infusing an appropriate solution, such as, for example, sterile saline and/or heparin, through the flushing port 176 of the hub 108, thereby eliminating any air bubbles 156 present in the catheter 100. Following placement of the intravascular catheter 100 in the body of a patient, and following placement of the device 152 in the intravascular catheter 100, air bubbles 156 introduced into the hub 108 of the intravascular catheter 100 may be aspirated from the hub 108 by attaching an appropriate device providing negative pressure to the flushing port 176 and aspirating the air bubbles 156 through the flushing port 176. Optionally, an appropriate solution, such as, for example, sterile saline and/or heparin, may then be infused through the flushing port 176 of the hub 108 into the reservoir 132.

In a further embodiment, the exemplary hub 108 is constructed from a transparent material, such as, for example, a transparent plastic. This feature advantageously permits direct observation of the air bubbles 156 trapped by the reservoir 132. By observing the trapped air bubbles 156, the physician is alerted to appropriately actuate the actuateable air release valve 172 and/or to aspirate the air bubbles 156 through the flushing port 176.

Figure 8:
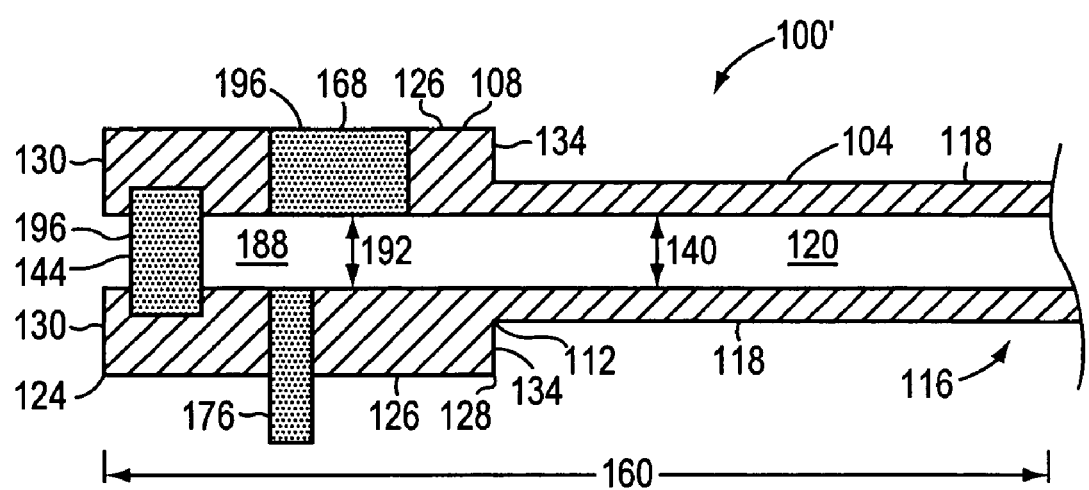
FIG. 8 is a schematic cross-sectional view of a portion of an intravascular catheter according to a further illustrative embodiment of the invention.

FIG. 8 depicts a portion of an intravascular catheter 100' according to still another illustrative embodiment of the invention. Generally speaking, except for the differences set forth below, the intravascular catheter 100' has substantially the same structure as the intravascular catheter 100 described above.

The illustrative embodiment of the intravascular catheter 100' shown in FIG. 8 eliminates the reservoir 132 of the catheter 100 illustrated in, for example, FIG. 1. As shown, the hub 108 of the intravascular catheter 100' substitutes a lumen 188 for the reservoir 132 described above. The lumen 188, unlike the reservoir 132 of the previous embodiments, has a cross-sectional diameter 192 that is substantially equal in size to the cross-sectional diameter 140 of the lumen 120 of the elongated tubular member 104. The lumen 188 of the hub 108 extends from the first end 124 of the hub 108 to the second end 128 of the hub 108 and is in fluid communication with the lumen 120 of the elongated tubular member 104. In one embodiment, the lumen 120 of the elongated tubular member 104 and the lumen 188 of the hub 108 are cylindrically-shaped and circular in cross-section. Alternatively, the lumen 120 of the elongated tubular member 104 and the lumen 188 of the hub 108 may be constructed to have any geometrical shape. The intravascular catheter 100' further includes at least one air permeable porous member 196.

As shown in FIG. 8, according to one embodiment of the invention, the intravascular catheter 100' includes two air permeable porous members 196, such as, for example, the air permeable membrane 168 and the first sealing gland 144. Alternatively, the intravascular catheter 100' includes one (e.g., only the air permeable membrane 168 or only the first sealing gland 144), three, or more air permeable porous members 196. In yet another embodiment, the entire hub 108 is constructed of an air permeable porous member 196, such that the entire hub 108 is breathable to air.

In one embodiment, the air permeable porous member 196 is fabricated from a porous material that allows introduced air bubbles 156 to passively exit (i.e., without physician intervention) through the pores into the surrounding environment outside the patient. The air permeable porous member 196 does not allow, however, any blood to exit therethrough. Specifically, the pore sizes of the air permeable porous member 196 are smaller than the size of red blood cells or white blood cells, but larger than the air molecules forming the air bubbles 156. In particular, the pore sizes may be in the range of about 0.01 μm to about 4.0 μm, preferably about 0.1 μm to about 1.0 μm. The porous material from which the air permeable porous member 196 is fabricated may be any polymer foam fabricated from material such as silicone, polyurethane, and/or a thermoplastic elastomer (e.g., styrene-ethylene-butadiene-styrene (SEBS)). Alternatively, the porous material from which the air permeable porous member 196 is fabricated may be any polymer film or fabric, such as, for example, woven or knitted polyester, expanded polytetrafluoroethylene (ePTFE) (i.e., GORE-TEX®), polyethyle-ter-aphalate film, polyethylene film, and/or polyvinyl alcohol (PVA) film.

In another embodiment, the air permeable porous member 196 is coated with or impregnated with a low thrombogenicity material. For example, the air permeable porous member 196 may be coated and/or impregnated with heparin, hyaluronic acid, and/or another anti-thrombotic coating, agent, mammalian genetic and recombinant genetic material, or drug.

In another aspect, the invention provides a method for introducing a device, such as, for example, another catheter (e.g., an angiocatheter), a stent, a filter, a septal occluder, a device for obliterating the left atrial appendage, a suture, a staple, or an adhesive, into the body of a patient through the intravascular catheter 100 or 100' according to the invention. In operation, the physician inserts the intravascular catheter 100 or 100' into a vessel of the patient, such as, for example, a patient's femoral vein or femoral artery. In one embodiment, the intravascular catheter 100 or 100' is inserted such that the long axis 160 of a proximal portion of the intravascular catheter 100 or 100' is substantially horizontal. The physician then inserts the device 152 into the hub 108 and advances the device 152 into the lumen 120 of the elongated tubular member 104. As described above, air bubbles 156 introduced into the hub 108 by inserting the device 152 therein are impeded from migrating distal to the second end 128 of the hub 108 and into the lumen 120 of the elongated tubular member 104. Specifically, as described above, the air bubbles 156 are impeded from migrating into the lumen 120 of the elongated tubular member 104 and/or caused to exit into the surrounding environment outside the patient by any one of, or combination of, a reservoir 132, a pocket 138, an air release valve 172, an air permeable membrane 168, a porous first sealing gland 144, a flushing port 176, and/or a second sealing gland 148 that is impermeable to air. As such, in accordance with the method of the invention, the device 152 may be inserted into the indwelling intravascular catheter 100 or 100' and itself delivered, or used to deliver another device, into the patient's vascular system without also introducing air into the patient's vascular system. Adverse consequences, such as, for example, acute pulmonary embolism, myocardial infarction, stroke, and possibly death, are, therefore, avoided.

Variations, modifications, and other implementations of what is described herein will occur to those of ordinary skill in the art without departing from the spirit and the scope of the invention. The invention is not to be defined only by the preceding illustrative description.

What is claimed is:

1. A method for inserting an intravascular catheter into the body of a patient, comprising:
   providing the intravascular catheter comprising:
   an elongated tubular member comprising a proximal end, a distal end, and a lumen extending from the proximal end to the distal end; and
   a hub comprising a first end, a second end, and a reservoir extending from the first end of the hub to the second end of the hub, the reservoir comprising at least one pocket that is partially shielded from the lumen of the elongated tubular member by a hub extension, the hub extension being an incomplete partition that extends from the second end of the hub into the reservoir in a direction towards the first end of the hub, wherein the second end of the hub is coupled to the proximal end of the elongated tubular member, and the first end of the hub comprises a first sealing gland, the first sealing gland comprising a plurality of air permeable pores that release air bubbles trapped in the reservoir into a surrounding environment outside the patient;
   inserting the intravascular catheter into a vessel of the patient; and
   inserting a second device through said intravascular catheter after inserting the intravascular catheter.

2. The method of claim 1, wherein at least a portion of the hub reservoir comprises a cross-sectional diameter greater in size than a cross-sectional diameter of the lumen of the elongated tubular member.

3. The method of claim 1, wherein the hub further comprises an air release valve that releases air bubbles trapped in the reservoir into a surrounding environment outside the patient.

4. The method of claim 1, wherein the hub further comprises an air permeable membrane that releases air bubbles through an external surface of the hub.

5. The method of claim 4, wherein the external surface is a side wall of the hub between the first end of the hub and the second end of the hub.

6. The method of claim 4, wherein the air permeable membrane is positioned through the external surface of the hub at at least one of the first end and the second end of the hub.

7. The method of claim 4, wherein the air permeable porous membrane comprises a low thrombogenicity material.

8. The method of claim 7, wherein the low thrombogenicity material comprises heparin.

9. The method of claim 7, wherein the low thrombogenicity material comprises hyaluronic acid.

10. The method of claim 1, wherein the hub further comprises a transparent material.

11. The method of claim 1, wherein the hub further comprises a flushing port.

12. The method of claim 1, wherein the hub further comprises an opening at the first end of the hub and wherein the opening is in fluid communication with the hub reservoir.

13. The method of claim 1, wherein the first end of the hub includes an opening, and the opening is in fluid communication with the reservoir through the first sealing gland.

14. The method of claim 1, wherein the second end of the hub comprises a second sealing gland.

* * * * *